US012661428B2

(12) United States Patent
Guo et al.

(10) Patent No.: US 12,661,428 B2
(45) Date of Patent: Jun. 23, 2026

(54) PREPARATION METHOD FOR NON-SPHERICAL HYDROGEL MICROPARTICLE EMBOLIC AGENT

(71) Applicant: Southern University of Science and Technology, Shenzhen (CN)

(72) Inventors: Qiongyu Guo, Shenzhen (CN); Yucheng Luo, Shenzhen (CN); Xingyu Jiang, Shenzhen (CN)

(73) Assignee: Southern University of Science and Technology, Shenzhen (CN)

( * ) Notice: Subject to any disclaimer, the term of this patent is extended or adjusted under 35 U.S.C. 154(b) by 803 days.

(21) Appl. No.: 17/588,344

(22) Filed: Jan. 31, 2022

(65) Prior Publication Data

US 2022/0160930 A1 May 26, 2022

Related U.S. Application Data

(63) Continuation of application No. PCT/CN2020/104781, filed on Jul. 27, 2020.

(30) Foreign Application Priority Data

Aug. 2, 2019 (CN) .......................... 201910716282.8

(51) Int. Cl.
| | |
|---|---|
| A61L 24/06 | (2006.01) |
| A61L 24/00 | (2006.01) |
| C08J 3/075 | (2006.01) |
| C08J 3/24 | (2006.01) |

(52) U.S. Cl.
CPC ........... *A61L 24/06* (2013.01); *A61L 24/0031* (2013.01); *C08J 3/075* (2013.01); *C08J 3/241* (2013.01)

(58) Field of Classification Search
CPC ....... C08J 3/075; C08J 3/13; C08J 3/24; C08J 3/241; C08F 16/06; C08F 116/06; C08L 29/04; B81B 2201/05051; B81B 2201/05; B81B 2201/051; A61L 24/06; A61L 24/046; A61L 24/0031
See application file for complete search history.

(56) References Cited

FOREIGN PATENT DOCUMENTS

| | | |
|---|---|---|
| CN | 102068409 A | 5/2011 |
| CN | 104173294 A | 12/2014 |
| CN | 104588139 A | 5/2015 |
| CN | 104829850 A | 8/2015 |

(Continued)

OTHER PUBLICATIONS

Partial machine translation of KR-101666789-B1 (Year: 2016).*

(Continued)

*Primary Examiner* — Kregg T Brooks

(57) ABSTRACT

A preparation method for a non-spherical hydrogel microparticle embolic agent is provided. The method includes: alternately injecting a oil phase solution and an aqeuous phase solution into an elongated channel, the aqueous phase solution contains a water-soluble polymer to be cross-linked, the aqueous phase solution has a cross-linking reaction in the elongated channel to obtain a product, which is then discharged from the elongated channel to obtain the non-spherical hydrogel microparticle embolic agent. This preparation method is simple in process, and the non-spherical hydrogel microparticle embolic agent obtained from this method has good embolization performance.

15 Claims, 3 Drawing Sheets

Provide an aqueous phase solution, an oil phase solution, and an elongated channel, where the aqueous phase solution includes a water-soluble polymer to be cross-linked —S110

Alternately inject the oil phase solution and the aqueous phase solution into the elongated channel to allow the aqueous phase solution to undergo a cross-linking reaction in the elongated channel to obtain a product —S120

Discharge the cross-linked intermediate/product from the elongated channel to obtain a non-spherical hydrogel microparticle embolic agent —S130

(56) References Cited

FOREIGN PATENT DOCUMENTS

| | | | |
|---|---|---|---|
| CN | 106947019 A | | 7/2017 |
| CN | 109482111 A | | 3/2019 |
| CN | 109821056 A | | 5/2019 |
| CN | 110585476 A | | 12/2019 |
| EP | 1295180 A2 | | 3/2003 |
| EP | 2556883 A1 | | 2/2013 |
| KR | 101666789 B1 | * | 10/2016 |
| WO | 2017208020 A2 | | 12/2017 |

OTHER PUBLICATIONS

Espacenet partial machine translation of KR 10-1666789 B1 (Year: 2016).*

International Search Report of PCT/CN2020/104781 (Oct. 27, 2020).

Shengqing Xu, Zhihong Nie et al., "Generation of Monodisperse Particles by Using Microfluidics: Control over Size, Shape, and Composition", Particle Design, vol. 44, No. 5, Dec. 31, 2005, entire document.

Xiao, Ai, "Microfluidic One-step Preparation of Magnetic Poly(Vinyl Alcohol) Microspheres and Their Applications in Interventional Embolization Therapy", Chinese Master's Theses Full-text Database, Nov. 30, 2017, p. 28, paragraph 1 to p. 32, last paragraph.

Qin Wang, Di Zhang et al., "Atom-economical in situ synthesis of BaSO4 as imaging", Green Chemistry, Dec. 31, 2013, entire document.

Qin Wang, Di Zhang et al., "Microfluidic one-step fabrication of radiopaque alginate microgels with in situ", Lab on a Chip, Nov. 21, 2012, entire document.

Shape-Controlled Production of Biodegradable Calcium Alginate Gel Microparticles Using a Novel Microfluidic Device", Kan Liu," Langmuir, vol. 22, No. 22, pp. 9453-9457, Oct. 24, 2006.

* cited by examiner

| Provide an aqueous phase solution, an oil phase solution, and an elongated channel, where the aqueous phase solution includes a water-soluble polymer to be cross-linked | S110 |
|---|---|
| Alternately inject the oil phase solution and the aqueous phase solution into the elongated channel to allow the aqueous phase solution to undergo a cross-linking reaction in the elongated channel to obtain a product | S120 |
| Discharge the cross-linked intermediate/product from the elongated channel to obtain a non-spherical hydrogel microparticle embolic agent | S130 |

FIG. 1

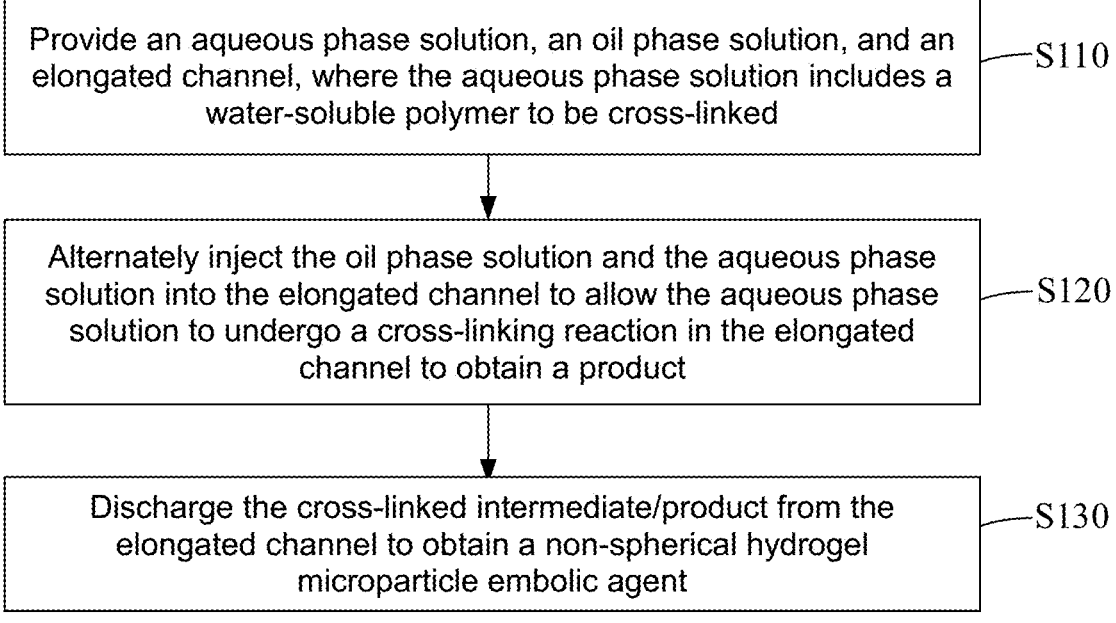

FIG. 2

PREPARATION METHOD FOR NON-SPHERICAL HYDROGEL MICROPARTICLE EMBOLIC AGENT

RELATED APPLICATIONS

This application is a continuation application of PCT application No. PCT/CN2020/104781, filed on Jul. 27, 2020, which claims the benefit of priority to Chinse Application No. 201910716282.8, filed on Aug. 2, 2019, and the contents of the foregoing documents are incorporated herein by reference in their entirety.

TECHNICAL FIELD

The present disclosure relates to the field of biomedicine, in particular to a preparation method for a non-spherical hydrogel microparticle embolic agent.

BACKGROUND

Liver cancer is a common cancer in the world. Transarterial chemoembolization (TACE) is a preferred strategy for the treatment of advanced liver cancer. The embolic agent used for transarterial chemoembolization may be made from a variety of materials, such as polylactic acid, polyvinyl alcohol (PVA), gelatin, chitosan, and the like. Polyvinyl alcohol has been widely used in many biomedical fields due to its good biocompatibility, non-toxicity and excellent gel-forming properties, such as the fields of bone tissue repair materials, drug delivery, vascular embolic agents, etc.

At present, the common process for preparing polyvinyl alcohol embolic agents is an emulsification method, that is, an emulsion of a polyvinyl alcohol solution in an oil phase is first formed to generate spherical droplets of polyvinyl alcohol, and then the droplets are solidified. In such an emulsion system, the polyvinyl alcohol solution is a dispersed phase, and another organic substance Immiscible with the polyvinyl alcohol aqueous solution is a continuous phase. During the emulsification process, the polyvinyl alcohol aqueous solution is added dropwise into an oil phase solution, and the polyvinyl alcohol solution is dispersed into the oil phase by magnetic stirring. The polyvinyl alcohol solution thus forms spherical droplets under an interfacial tension. These droplets are then solidified into microspheres by various cross-linking ways and separated from the oil phase. However, this method is limited to the preparation of spherical embolic agents, yet the embolic properties of spherical embolic agents are undesirable. Currently, the non-spherical embolic agent is obtained by using the method of stretching a body to be stretched. However, this method has complicated procedures.

BRIEF SUMMARY

In view of the foregoing, it is necessary to provide a method for preparing a non-spherical hydrogel particle embolic agent with a simple process.

In a first aspect, the present disclosure provides a preparation method for an elongated non-spherical hydrogel microparticle embolic agent, including: obtaining an aqueous phase solution dissolved with a polymer to be cross-linked; obtaining an oil phase solution dissolved with a water-soluble cross-linking agent; alternately injecting the oil phase solution and the aqueous phase solution into an elongated channel to allow the aqueous phase solution to form long droplets in the elongated channel and allow the water-soluble cross-linking agent in the oil phase solution to diffuse from the oil phase solution into the long droplets, such that the water-soluble cross-linking agent and the polymer in the long droplets have a cross-linking reaction in the elongated channel to obtain a solidified elongated non-spherical hydrogel microparticle embolic agent with stable shape; and discharging the embolic agent from the elongated channel.

According to the preparation method of the non-spherical hydrogel microparticle embolic agent of the present disclosure, a water phase solution and an oil phase solution are injected into an elongated channel to have a cross-linking reaction in the elongated channel, and then a product of the reaction is discharged therefrom, so that the obtained embolic agent has a regular non-spherical structure. Its process is simple. For the method for obtaining an elongated embolic agent through a stretching process, it needs to first prepare a to-be-stretched body, then obtain a to-be-stretched film from the to-be-stretched body, and finally perform the stretching process. Thus, the steps are cumbersome. Therefore, the preparation method of the present disclosure is simple, and can obtain the non-spherical hydrogel microparticle embolic agent.

BRIEF DESCRIPTION OF THE DRAWINGS

To describe the technical solutions in the embodiments of the present disclosure, the following briefly describes the accompanying drawings required for describing some exemplary embodiments of the present disclosure. Apparently, the accompanying drawings in the following description show merely some exemplary embodiments of the present disclosure, and a person of ordinary skill in the art may still derive other drawings from these accompanying drawings without creative efforts.

FIG. 1 is a flow chart of a preparation method of a non-spherical hydrogel microparticle embolic agent according to some exemplary embodiments;

FIG. 2 is a schematic structural diagram of a microfluidic chip according to some exemplary embodiments;

FIGS. 4A and 4B show different arrangements of the non-spherical hydrogel microparticle embolic agent, FIGS. 4C and 4D are fluorescence images corresponding to FIGS. 4A and 4B, respectively.

DETAILED DESCRIPTION

Figure 3A:
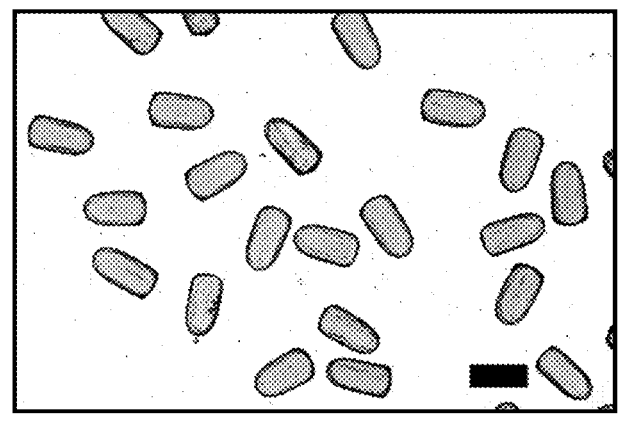
FIGS. 3A, 3B and 3C are microscopic images of a non-spherical hydrogel microparticle embolic agent observed under a microscope according to some exemplary embodiments.
Figure 3B:
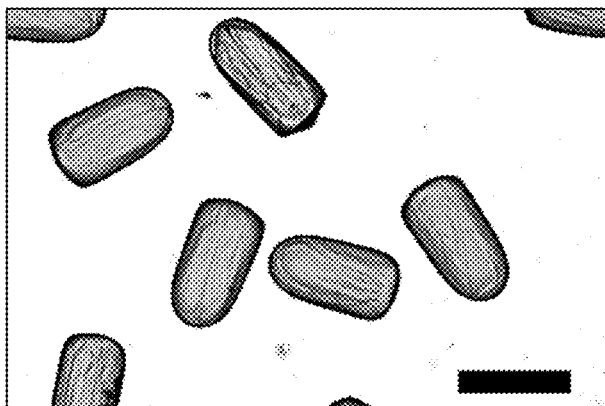
Figure 3C:
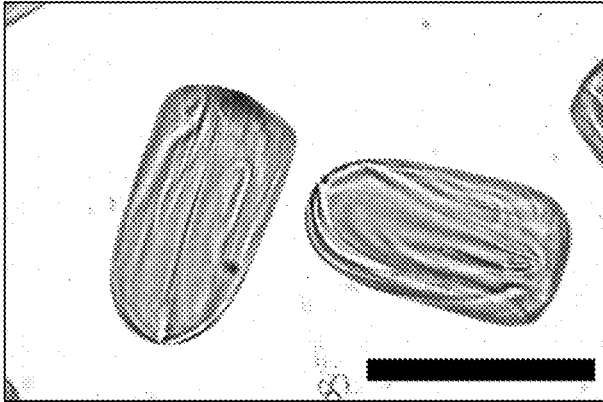

To facilitate the understanding of the present disclosure, the present disclosure will be described in detail below with reference to certain exemplary embodiments. Some exemplary embodiments are described below. However, the present disclosure is not limited to these exemplary embodiments. These exemplary embodiments are provided to facilitate understanding of the present disclosure.

Unless otherwise defined, all technical and scientific terms used herein have the same meaning as commonly understood by a person skilled in the art to which the present disclosure pertains. The terminology used herein is for the purpose of describing some exemplary embodiments and is not intended to limit the present disclosure.

It should be noted that a geometric of an object usually contains 3 principal semi-axes. For example, an ellipsoid may include 3 principal semi-axes a, b, and c, where a>b>c. Accordingly, the non-spherical hydrogel microparticle in the present disclosure has at least 2 of the 3 semi-axes different from each other, and for an elongated non-spherical hydrogel in the present disclosure may refer to a non-spherical object that has one semi-axis substantially longer than the other two semi-axes.

In the present disclosure an elongated channel refers to a channel of which a ratio between its length and width is greater than 10 and less than 10,000. However, the ratio may also be less than 10 or greater than 10,000 as needed, which is not limited herein.

FIG. 1 is a flow chart of a preparation method of a non-spherical hydrogel microparticle embolic agent according to some exemplary embodiments. As shown in FIG. 1, the method may include the following steps.

Step S110: provide an aqueous phase solution, an oil phase solution, and an elongated channel, where the aqueous phase solution includes a water-soluble polymer to be cross-linked.

In this step, the aqueous phase solution may further include a catalyst. In some exemplary embodiments, in the aqueous phase solution, a mass fraction of the water-soluble polymer may be within a range of 2.5% to 7.5% and a concentration of the catalyst may be within a range of from 0.25 mol/L to 0.75 mol/L. For example, the mass fraction of the water-soluble polymer may be 2.5%, 3%, 3.5%, 4%, 4.5%, 5%, 5.5%, 6%, 6.5%, 7%, or 7.5%, or a value between any two forgoing mass fraction values. The mass fraction of the water-soluble polymer may also be a value lower than 2.5%, or a value higher than 7.5%, etc. Similarly, the concentration of the catalyst may be 0.25 mol/L, 0.3 mol/L, 0.35 mol/L, 0.4 mol/L, 0.45 mol/L, 0.50 mol/L, 0.55 mol/L, 0.60 mol/L, 0.65 mol/L, 0.70 mol/L, or 0.75 mol/L, or may be a value between any of the forgoing concentration values. The concentration of the catalyst may also be a value lower than 0.25%, or a value higher than 0.75%, etc. However, it is noted that the foregoing ranges are exemplary, and based on the specific materials used and the properties and performance thereof, various materials may have different ranges, which may be within the range mentioned above, or may be beyond these ranges. Also, the water-soluble polymer may include, but is not limited to, polyvinyl alcohol, polyethylene glycol, a polyvinyl alcohol-based copolymer, a polyethylene glycol-based copolymer, and the like. However, the present disclosure is not limited to the above examples. Compounds with similar structures or properties may also be used, which is not limited herein. In some exemplary embodiments, the water-soluble polymer may be polyvinyl alcohol, the catalyst may be hydrochloric acid or sulfuric acid, and the cross-linking agent may be glutaraldehyde.

The polyvinyl alcohol molecule contains a large number of hydroxyl groups, and is a water-soluble material. It may be prepared into microsphere embolic agents through a physical cross-linking process (such as a freeze-thaw process), an ultraviolet cross-linking process (the polyvinyl alcohol molecule needs to be modified beforehand to obtain a photosensitive group), or a chemical cross-linking process (such as glutaraldehyde cross-linking, boric acid cross-linking, etc.). Among these processes, cross-linking polyvinyl alcohol with glutaraldehyde is an efficient, simple, and easy-to-operate cross-linking process. The reaction of cross-linking polyvinyl alcohol with glutaraldehyde may occur under heating and acidic conditions. After glutaraldehyde and polyvinyl alcohol molecules are cross-linked, water-soluble polyvinyl alcohol molecules can form a gel or a solid.

As mentioned previously, it is understood that in some embodiments, the water-soluble polymer, cross-linking agent, etc. can also be other substances, which are not limited herein. Moreover, in addition to glutaraldehyde, the cross-linking agent may also be, but is not limited to, formaldehyde, an organic acid, such as, citric acid, malonic acid, oxalic acid, trimellitic acid, polyacrylic acid, fumaric acid, amic acid, etc., maleic anhydride, and the like, which is also not limited herein.

The aqueous phase solution may be prepared by any suitable method. For example, a water-soluble polymer solution with a mass fraction of 10% may be mixed with a catalyst to obtain an aqueous phase solution. In this case, a concentration of the catalyst may be 1 mol/L. A volume ratio of the water-soluble polymer solution to the catalyst may be from 1:3 to 3:1. For example, the volume ratio of the water-soluble polymer solution to the catalyst may be 1:3, 1:2, 1:1, 2:1, 3:1, or a value between any of the forgoing 2 ratios. It is noted that the preparation of the aqueous phase solution is not limited to the example provided above. The specific substances (polymer, catalyst, etc.), the concentrations, volumes and ratios thereof may be changed as needed.

The oil phase solution may contain an oil-based solvent, a lipophilic emulsifier, and a cross-linking agent. A mass ratio of the oil-based solvent, the lipophilic emulsifier and the cross-linking agent may be 1:x:y with reference to the oil-based solvent. The value of x may be in a range of (0.01-0.04) and the value of y may be in a range of (0.075-0.3). For example, the value of x may be any of 0.015, 0.020, 0.025, 0.030, 0.035, 0.040, or a value between any 2 forgoing values; the value of y may be an of 0.075, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, or a value between any 2 forgoing values. Similarly, the specific substances of the oil-based solvent, the lipophilic emulsifier, and the cross-linking agent, as well as their ratios are not limited in the present disclosure. The oil-based solvent may be able to dissolve the cross-linking agent. Specifically, the preparation of the oil phase solution may include: mixing the oil-based solvent, the lipophilic emulsifier and a cross-linking agent in a mass ratio of 1:x:y 1:(0.01−0.04):(0.075−0.3) with reference to the oil-based solvent, and then stirring to obtain an oil phase solution. The foregoing is merely an example, and the preparation of the oil phase solution is not limited to this example.

In some exemplary embodiments, the oil-based solvent may be soybean oil. However, the oil-based solvent may also be liquid paraffin, dimethicone, or the like. It is understood that any oil-based solvent capable of dissolving the cross-linking agent may be used as the oil-based solvent in the present disclosure.

The lipophilic emulsifier may be a sorbitan fatty acid ester, such as span-80. However, it is understood that other lipophilic emulsifiers may also be used in the present disclosure.

Moreover, the preparation of the oil phase solution may further include a heating step. The oil-based solvent, the lipophilic emulsifier and the cross-linking agent may be sufficiently dissolved by heating. Specifically, the heating temperature may be from 60° C. to 85° C. It is desired to allow the lipophilic emulsifier and the cross-linking agent to be sufficiently dissolved in the oil phase solution by heating. However, the sufficient dissolution may be achieved in other ways than heating. In addition, the heating range of from 60° C. to 85° C. is merely an example. Any suitable temperature range may be employed in the present disclosure as needed. For example, the heating temperature may be within a range between any two of the following values: 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., a temperature lower than 60° C., and a temperature higher than 85° C.

The preparation step of the oil phase solution may further include a step of centrifugation and then taking the resulting supernatant.

In some exemplary embodiments, the depth and width of the elongated channel may be less than 1 mm. The depth and width of the elongated channel may have an influence on the width of the embolic agent prepared, In general, the greater the depth and width of the elongated channel, the greater the width of the embolic agent. The size of the embolic agents commonly used in clinical practice is within 1 mm. Hence, the width and depth of the elongated channel may be set as less than 1 mm. However, according to the actual practices, the width and depth of the elongated channel may also be equal to or even greater than 1 mm, which is not limited herein.

In some exemplary embodiments, the elongated channel may include an inlet end and an outlet end. The aqueous phase solution and the oil phase solution may be loaded (such as injected, etc.) into the elongated channel from the inlet end; the aqueous phase solution undergoes a cross-linking reaction in the I elongated channel, and then the aqueous phase solution flows out of the elongated channel via the outlet end.

In some exemplary embodiments, the elongated channel may be disposed in a microfluidic chip. The microfluidic chip may include an inlet end and an outlet end. The material of the microfluidic chip may be a hydrophobic material. In some exemplary embodiments, the material of the microfluidic chip may be quartz. The material of the microfluidic chip may also be other hydrophobic materials, such as glass-based capillary. In the case where the microfluidic chip is made from a hydrophobic material, the water-soluble polymer solution may be prevented from adhering to a wall of the channel, thereby facilitating the generation of water-in-oil droplets.

In some exemplary embodiments, the microfluidic chip may be provided with a first inlet opening, a second inlet opening and an outlet opening, the first inlet opening and the second inlet opening may be arranged at the inlet end, and the outlet opening may be arranged at the outlet end. The elongated channel may include a first passage, a second passage and a third passage. The first passage may be in communication with the first inlet opening, the second passage may be in communication with the second inlet opening, and the third passage may be in communication with the outlet opening. In addition, an end of the first passage away from the first inlet opening, an end of the second passage away from the second inlet opening and an end of the third passage away from the outlet opening may intersect and communicate with each other. The oil phase solution and the aqueous phase solution may be injected into the first passage and the second passage respectively via the first inlet opening and the second inlet opening, and a cross-linking reaction may occur in the third passage.

In some exemplary embodiments, as shown in FIG. 2, the microfluidic chip 200 may have an elongated channel. The elongated channel may include a first passage 220 and a second passage 240 in a "Y"-shaped structure. The first passage 220, the second passage 240 and the third passage 260 intersect and communicate with each other. The third passage 260 may include an arched channel 262, and a straight channel 264 in communication with the arched channel 262. One end of the arched channel 262 away from the straight channel 264 and one end of the first passage 220 away from the first inlet opening 202, an end of the second passage 240 away from the second inlet opening 204 may intersect and communicate with each other, and the straight channel 264 may communicate with the outlet opening 206.

As shown in this figure, the arched channel 262 may include ten wave bends. The purpose of providing the arched channel 262 in the elongated channel is to extend the distance to allow the mixed aqueous phase solution and oil phase solution to be sufficiently cross-linked in the arched channel 262, thereby reducing the length of the straight channel 264 and reducing the size of the microfluidic chip 100. It is understood that the number of wave bends herein is not limited to ten, and may also be eight, nine, eleven, or any number as needed. In addition, in some exemplary embodiments, the arched channel 262 may be omitted. In such a case, an intersection of the first passage 220 and the second passage 240 may be in direct communication with the straight channel 264. After the aqueous phase solution and the oil phase solution are mixed, they may be fully cross-linked in the straight channel 264.

The preparation of the microfluidic chip may include: forming a first passage, a second passage and a third passage on a hydrophobic sheet, forming the first passage, the second passage and the third passage on a surface of a polydimethylsiloxane (PDMS) glue through molding, and then bonding the surface and the hydrophobic sheet through the plasma technology to obtain the microfluidic chip.

Microfluidics is a technology that controls droplet generation, droplet mixing, and particle preparation. The generation of spherical droplets may be implemented using microfluidic chips. In addition, the microfluidic chip can easily produce various emulsion systems, including, but not limited to, oil-in-water (O/W), water-in-oil (W/O), water-in-oil-in-water (W/O/W), oil-in-water-in-oil (O/W/O), etc. Moreover, the microfluidic chip may precisely control the size of the droplets and may continuously generate the same droplets in large quantities. Thus, it has great advantages in applications in droplet synthesis and particle preparation. In some exemplary embodiments, the employment of a microfluidic chip may allow the obtained embolic agent to have substantially uniform shape and size. In addition, the size of the embolic agent may be adjusted by adjusting the width and depth of the channel(s) in the microfluidic chip.

Step S120: alternately inject the oil phase solution and the aqueous phase solution into the elongated channel to allow the aqueous phase solution to undergo a cross-linking reaction in the elongated channel to obtain a product (e.g., a cross-linked product).

In some exemplary embodiments, in the step in which the aqueous phase solution undergoes a cross-linking reaction in the elongated channel, the cross-linking reaction may be a thermal cross-linking reaction. It is understood that, the cross-linking reaction may also be carried out in other processes, such as a photo-cross-linking, etc. This is not limited in the present disclosure.

In some exemplary embodiments, the microfluidic chip may have the structure shown in FIG. 2, and the step S120 may include: alternately inject the oil phase solution and the aqueous phase solution into the first passage and the second passage through the first inlet opening and the second inlet opening respectively to allow the aqueous phase solution to undergo a cross-linking reaction in the third passage.

In some exemplary embodiments, the step of injecting the oil phase solution and the aqueous phase solution into the first passage and the second passage via the first inlet opening and the second inlet opening respectively may include: drawing the oil phase solution and the aqueous phase solution into separate syringes, where one end of each syringe may be mounted to a microinjector, and an end of each syringe away from the microinjector may be connected to a silicone hose; an end of each silicone hose away from the syringe may be connected to a steel pipe, and the two steel pipes are respectively in communication with the first inlet opening and the second inlet opening of the microfluidic chip. The microinjectors are first turned on to respectively inject the oil phase solution and the aqueous phase solution into the first inlet opening and the second inlet opening through the corresponding syringes, silicone hoses and steel pipes at a flow ratio of 20:1 to 2:1, which then enter the first passage and the second passage, respectively.

It is understood that, the oil phase solution and the aqueous phase solution may be loaded into the first passage and the second passage of the microfluidic chip in other ways, and the flow rate and the flow ratio may be changed as needed. The flow ratio of 20:1 to 2:1 is exemplary. This ratio may be within any range as needed, which is not limited herein. For example, the flow ratio may be 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, or 2:1.

Subsequently, a part of the silicone hose for oil phase solution injection may be immersed in hot water at a first predetermined temperature, e.g., 65° C., to heat the oil phase solution. The length of the silicone hose immersed in hot water may ensure that the oil phase solution is heated to a second predetermined temperature, e.g., above 40° C. In some exemplary embodiments, the length of the silicone hose for oil phase solution injection may be 125 cm, and the length of the silicone hose immersed in hot water may be from 90 cm to 110 cm, so that the oil phase solution may be heated to the second predetermined temperature, e.g., above 40° C. It is noted that although water heating has advantages, in the present disclosure, the hose may be heated in other thermal media or in other ways as needed by specific practices. Moreover, the temperatures provided above are example, which can be any suitable temperatures, for example, the oil phase solution may be heated to a suitable temperature equal to or lower than 40° C., such as 39° C., 38° C., 37° C., 36° C., 35° C., etc.; alternatively, the oil phase solution may be heated to a suitable temperature higher than 40° C., such as 42° C., 44° C., 46° C., 48° C., 50° C., etc. Moreover, the length of the hose and the portion of the hose immersed in water or other media are not limited in the present disclosure, which may be any length as needed.

At the intersection between the first passage and the second passage in the microfluidic chip, the aqueous phase solution meets the oil phase solution. Because the oil phase solution contains a lipophilic emulsifier that facilitates the dispersion of the aqueous phase solution, the viscosity and flow rate of the of the oil phase are relatively high, the aqueous phase solution may be cut into droplets of a certain length. The droplets may be of a size larger than the cross section of the third passage, so that the droplets may be squeezed by the sidewalls of the third passage to form long droplets when entering the third passage. After the long droplets are formed, they may be solidified in the third passage (for example, the cross-linking agent diffused from the oil phase may have a cross-linking reaction with the water-soluble polymer droplets), and then discharged from the outlet opening. For example, during traveling in the third passage, because the cross-linking agent dissolved in the oil-based solvent may also be water soluble, it may diffuse from the oil-based solvent into the aqueous phase solution, and thereby solidify the polymer to be cross-linked. Further, the environment of reaction (reaction temperature and reaction time in the third passage) may be sufficient enough to allow the polymer is sufficiently solidified, so that when discharged from the outlet opening, the solidified droplets may not experience substantial deformation and remain an elongated non-spherical shape.

In some exemplary embodiments, the ratio of the injection rate of the oil phase solution to the injection rate of the aqueous phase solution may be 20:1 to 2:1. For example, the ratio may be 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, or 2:1. By controlling the flow rates of the oil phase solution and the aqueous phase solution, the length of the non-spherical water-soluble polymer droplets may be regulated. Specifically, in some exemplary embodiments, the flow rate of the oil phase solution may be set as a first predetermined value, e.g., 20 μL/min, and the flow rate of the aqueous phase solution may be set as a second predetermined value, e.g., 1 μL/min to 10 μL/min (e.g., 1 μL/min, 2 μL/min, 3 μL/min, 4 μL/min, 5 μL/min, 6 μL/min, 7 μL/min, 8 μL/min, 9 μL/min, 10 μL/min, or any value between any 2 values of the foregoing value). Experiments show that when the flow rates of the oil phase solution and the water phase solution are as mentioned above and the width and height of the elongated channel are 0.5 mm, the length of the obtained non-spherical hydrogel microparticles embolic agent may be 385 μm to 840 μm, and the width thereof may be 290 μm to 330 μm, which means that the obtained non-spherical hydrogel microparticles are elongated non-spherical hydrogel microparticles, and during the cross-link reaction, the size of the hydrogel microparticles shrinks. It is noted that the foregoing values or ranges are exemplary, which are not limited in the present disclosure. For example, the injection rate ratio may also be any suitable ratio higher than 20:1 or lower than 2:1. In addition, the flow rates of the oil phase solution and the water phase solution can be any suitable values. Moreover, the dimensions of the obtained non-spherical hydrogel microparticle embolic agent are not limited to the values and ranges mentioned in the above example. There are many factors may affect the dimensions of the obtained embolic agent, such as the specific materials used, the concentrations thereof, the operating conditions such as flow rate, temperature, etc. As a result, the obtained embolic agent may have different dimensions tailored to meet the demands of various applications.

In step S120, the time of the cross-linking reaction between the oil phase solution and the aqueous phase solution in the elongated channel may be from 1.2 to 1.8 minutes, so that the oil phase solution and the aqueous phase solution are sufficiently cross-linked and solidified. In step S120, the flow rates of the oil phase solution and the aqueous phase solution may be further adjusted based on the reaction time and the total length of the third passage, so that the oil phase solution and the aqueous phase solution may sufficiently react in the third passage. It is noted that the reaction time may vary based on the materials in the reaction system and the reaction time, for example, the reaction time may be 1.2 minutes, 1.3 minutes, 1.4 minutes, 1.5 minutes, 1.6 minutes, 1.7 minutes, 1.8 minutes, a suitable time period longer than 1.8 minutes, or a suitable time period shorter than 1.2 minutes.

Step S130: Discharge the cross-linked product from the elongated channel to obtain the elongated non-spherical hydrogel microparticle embolic agent.

Specifically, because the environment of reaction (reaction temperature and reaction time in the third passage) may be sufficient enough to allow the polymer is sufficiently solidified, when discharged from the outlet opening, the solidified droplets may not experience substantial deformation and remain an elongated non-spherical shape. The step of discharging the product from the I elongated channel may include: immersing the outlet end in a collection solution, and heating and stirring the collection solution. The collection solution may include an oil-based solvent. Further, the collection solution may also include a cross-linking agent, so that the cross-linking agent may react with the cross-linked product to further cross-link the product obtained in S120. Moreover, a mass ratio of the oil-based solvent, the lipophilic emulsifier and the cross-linking agent in the collection solution may be 1:m:n, where m may be of a range of (0.02-0.08), and n may be of a range of (0.075-0.3). It is noted that the foregoing mass ratio range is exemplary; to obtain a desired embolic agent product from S130, the mass ratio range of the collection solution may be different as needed. For example, the value of m may be any of 0.020, 0.025, 0.030, 0.035, 0.040, 0.045, 0.050, 0.055, 0.060, 0.065, 0.070, 0.075, 0.08 or a value between any 2 forgoing values; the value of n may be an of 0.075, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, or a value between any 2 forgoing values.

The preparation of the collection solution may include: mixing the oil-based solvent, the lipophilic emulsifier and the cross-linking agent in a mass ratio of 1:(0.02–0.08): (0.075–0.3) and stirring, next centrifuging, and then taking the supernatant oil so as to obtain the collection solution. The oil-based solvent may dissolve the cross-linking agent. The collection solution may be used to sufficiently cross-link the water-soluble polymer by the cross-linking agent. The dose of the lipophilic emulsifier in the collection solution is higher than that in the oil phase solution, so as to prevent the generated embolic agent from sticking and agglomerating, thus the embolic agent is dispersed in the collection solution.

The step of immersing the outlet end in the collection solution, and heating and stirring the collection solution may be carried out under a heating condition, so that the cross-linking of the water-soluble polymer may be more sufficient. Specifically, the heating temperature may be from 40° C. to 85° C., and the stirring time may be from 1 h to 2 h. It is noted that both the heating temperature and the stirring time provided herein are exemplary, and are not limited in the present disclosure. The heating temperature in S130 may be within a range between any two temperatures of 40° C., 45° C., 50° C., 55° C., 60° C., 65° C., 70° C., 75° C., 80° C., 85° C., a suitable temperature lower than 40° C., and a suitable temperature higher than 85° C. Similarly, the stirring time may be 1 h, 1.5 h, 2 h, or any time period that is needed to achieve sufficient or suitable mixing or cross-linking result.

Specifically, after the procedure of immersing the outlet end in the collection solution and heating and stirring the collection solution, S130 may further include a centrifugal step and a washing step. In some exemplary embodiment, in the step of centrifugation, the rotation speed may be 2000 rpm, and the centrifugation time may be 2 minutes. The washing step may include four times of washing with acetone followed by three times of washing with water. The washing process may be accompanied by a shaking process, so that the impurities adhering to the embolic agent may be washed away. To obtain a desired result, the centrifugation speed and the time may be changed as needed, which is not limited in the present disclosure.

The preparation method of the non-spherical hydrogel microparticle embolic agent may have at least the following advantages.

(1) The preparation method of the non-spherical hydrogel microparticle embolic agent can obtain the non-spherical hydrogel microparticle embolic agent as described above. In addition, the length of the non-spherical hydrogel microparticle embolic agent may be regulated by changing the flow rate ratio of the oil phase solution to the aqueous phase solution.

(2) Compared with spherical embolic microspheres, the embolic agent obtained by the preparation method of the present disclosure may form an arrangement in blood vessels, is easier to aggregate, and may achieve a stable embolization effect. In addition, the non-spherical embolic agent may increase the contact area with the blood vessel wall, which may facilitate sustained release of a drug and cover a larger area of the drug release.

(3) In some traditional emulsion methods, during the process of forming the emulsion, the polyvinyl alcohol solution may not be uniformly dispersed in the oil phase even with magnetic stirring due to the high viscosity of the oil phase solution. This makes the obtained polyvinyl alcohol microspheres with lower specification uniformity. In addition, during the emulsification process, if the magnetic stirring is not sufficient, the polyvinyl alcohol solution may be deposited at the bottom of the oil phase solution, so that the generated polyvinyl alcohol microspheres may stick together into sheets. In contract, the embolic agent obtained by the preparation method of the present disclosure has more regular and uniform shape and size. Moreover, it does not easily aggregate in the oil phase solution, and can be easily separated.

(4) The preparation of polyvinyl alcohol microspheres by some traditional emulsification methods takes a long time and the product yield of each preparation is low, whereas the preparation method of non-spherical hydrogel particle embolic agent according to the present disclosure is simple to operate, and the embolic agent product be prepared in large scale.

(5) In some traditional methods, a process of stretching a product body to be stretched may be employed to make the aspect ratio of the body to be stretched to reach a specific value to obtain an embolic agent, However, in such a process, the body to be stretched needs to be prepared first, and then the body to be stretched is made into a film to be stretched, and finally the film is stretched. Thus, the steps are cumbersome, and it is difficult to ensure the regularity and uniformity of the obtained embolic agent. In contract, according to the preparation method provided in the present disclosure, the oil phase solution and the aqueous phase solution are cross-linked in an elongated channel during the preparation process, and then discharged therefrom. As a result, uniform non-spherical embolic agent may be obtained, and the operation is simpler.

Some specific examples and comparative examples will be provided below to further illustrate the present disclosure and exhibit its advantages. It is noted that each value and condition described in the following examples are exemplary, which do not limit the present disclosure. The weight-average molecular weight (Mw) of the polyvinyl alcohol (PVA) used in Examples 1 to 4 is 31,000 to 50,000, and the degree of polymerization thereof is 87% to 89%.

Example 1

The preparation process of the non-spherical hydrogel particle embolic agent in this example is as follows:

(1) Weigh 10 g of PVA solid into a beaker, add 90 g of pure water, heat and stir at 280 rpm for 3 h to dissolve PVA so as to obtain a 10 wt % PVA solution, mix the 10 wt % PVA solution with a 1 mol/L hydrochloric acid solution in a volume ratio of 1:1 to obtain an acidic polyvinyl alcohol solution, next add a small amount of rhodamine B dye for coloration so as to obtain an aqueous phase solution.

(2) Weigh soybean oil, span-80 and a 25 wt % glutaral-dehyde aqueous phase solution into a beaker at a mass ratio of 1:0.02:0.15, heat and stir at 52° C. and 280 rpm for half for 1 h, and then centrifuge at 2000 rpm for 3 min, collect the upper layer of oil so as to obtain an oil phase solution.

(3) Weigh soybean oil, span-80 and a 25 wt % glutaral-dehyde aqueous phase solution into a beaker at a mass ratio of 1:0.02:0.15, heat and stir at 52° C. and 280 rpm for half for 0.5 h, and then centrifuge at 2000 rpm for 3 min, collect the upper layer of oil so as to obtain a collection solution.

(4) Separately draw the oil phase solution and the aqueous phase solution into two 5 mL syringes, connect a needle of the syringe for the oil phase solution to a silicone hose with an inner diameter of 0.5 mm, and outer diameter of 2 mm and a length of 125 cm, connect a needle of the syringe for the aqueous phase solution to a silicone hose with an inner diameter of 0.5 mm, and outer diameter of 2 mm and a length of 65 cm, sleeve another end of each silicone hose over a capillary steel pipe with an outer diameter of 1 mm, then insert the capillary steel pipe corresponding to the oil phase solution to a first inlet opening of a microfluidic chip, and insert the capillary steel pipe corresponding to the aqueous phase solution to a second inlet opening of the microfluidic chip.

(5) Immerse a part of the silicone hose (90 cm) for the oil phase solution in a beaker filled with hot water at 65° C., where a length from an end of this silicone hose to the hot water is no more than 5 cm, place a beaker of hot water on a heated stirring device and set the temperature of the heated stirring device as 65° C., respectively connect two syringes with two microinjectors, set the flow rate of the oil phase solution as 20 μL/min, and set the flow rate of the aqueous phase solution as 4 μL/min.

(6) Immerse an outlet end of the microfluidic chip into the collection solution when the discharged non-spherical hydrogel particle embolic agent is stable and in an elongated shape (the outlet end of the microfluidic chip is slight below the top level of the collection solution), place the beaker containing the collection solution on the heated stirring device, and heat at 65° C. with stirring at 220 rpm.

Inject the oil phase solution and the aqueous phase solution respectively for 1 h according to the procedures previously described in the present disclosure, remove the microfluidic chip, continuously stir the collection solution at 65° C. and 220 rpm for 1 h, transfer the collection solution to a centrifuge tube, centrifuge at 2000 rpm for 2 min, and remove the top layer of oil to obtain a crude product.

Add an acetone solution to the crude product, shake and wash, and then centrifuge at 2000 rpm for 2 min to obtain a precipitate, add the acetone solution to the precipitate, repeat the washing and centrifugation steps four times, next add pure water, shake and wash, and then centrifuge at 2000 rpm for 2 min, add pure water and repeat the washing and centrifugation steps four times, so as to obtain a purified non-spherical hydrogel microparticle embolic agent (that is, a PVA embolic agent), and then store the purified non-spherical hydrogel microparticle embolic agent in pure water.

Figures 4A, 4B, 4C, 4D, 5:
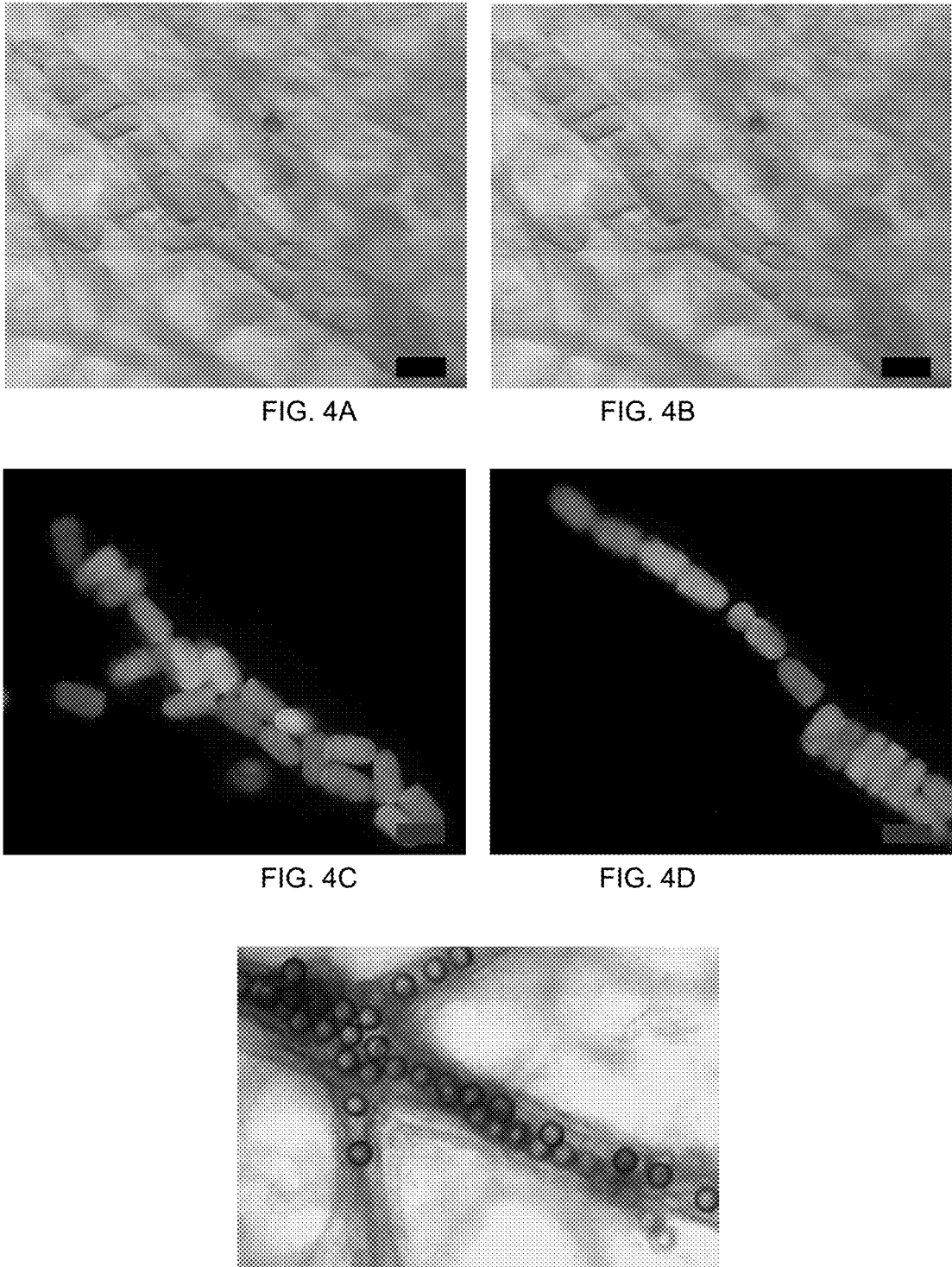
FIGS. 4A, 4B, 4C and 4D show an embolization effect of a non-spherical hydrogel microparticle embolic agent on a decellularized liver of rabbit according to some exemplary embodiments, among them.
FIG. 5 embolization effect of the spherical polylactic acid particle embolic agent on decellularized rat liver in some comparative examples.

The non-spherical hydrogel microparticle embolic agent obtained in Example 1 has been observed under a microscope, it is found that the length of the non-spherical hydrogel microparticle embolic agent is 580 μm and the width thereof is 310 μm, as shown in FIGS. 4A, 4B and 4C. The scale bars in the figures are all 500 μm.

Example 2

The preparation process of the non-spherical hydrogel microparticle embolic agent in Example 2 is similar to the preparation process in Example 1, with the following difference:

In step (5), the flow rate of the aqueous phase solution is set as 6 μL/min.

The non-spherical hydrogel microparticle embolic agent obtained in Example 2 has been observed under a microscope, it is found that the length of the non-spherical hydrogel microparticle embolic agent is 620 μm and the width thereof is 310 μm.

Example 3

The preparation process of the non-spherical hydrogel microparticle embolic agent in Example 3 is similar to the preparation process in Example 1, with the following difference:

In step (1), 10 wt % PVA solution and 1 mol/L hydrochloric acid solution are mixed in a volume ratio of 1:3.

In step (2), soybean oil, span-80 and a 25% glutaraldehyde aqueous phase solution are weighed according to a mass ratio of 1:0.01:0.075, and added to a beaker.

In step (3), soybean oil, span-80 and a 25% glutaraldehyde aqueous phase solution are weighed according to a mass ratio of 1:0.02:0.075, and added to a beaker.

In step (5), the flow rate of the aqueous phase solution is 2 μL/min.

The non-spherical hydrogel microparticle embolic agent obtained in Example 3 has been observed under a microscope, it is found that the length of the non-spherical hydrogel microparticle embolic agent is 590 μm and the width thereof is 450 μm.

Example 4

The preparation process of the non-spherical hydrogel microparticle embolic agent in Example 4 is similar to the preparation process in Example 1, with the following difference:

In step (1), 10 wt % PVA solution and 1 mol/L hydrochloric acid solution are mixed in a volume ratio of 3:1.

In step (2), soybean oil, span-80 and a 25% glutaraldehyde aqueous phase solution are weighed according to a mass ratio of 1:0.04:0.075, and added to a beaker.

In step (3), soybean oil, span-80 and a 25% glutaraldehyde aqueous phase solution are weighed according to a mass ratio of 1:0.08:0.075, and added to a beaker.

In step (5), the flow rate of the aqueous phase solution is 10 μL/min.

The non-spherical hydrogel microparticle embolic agent obtained in Example 3 has been observed under a microscope, it is found that the length of the non-spherical hydrogel microparticle embolic agent is 740 μm and the width thereof is 308 μm.

Comparative Example 1

The preparation process of a spherical polylactic acid embolic agent in Comparative Example 1 is as follows:

Prepare polylactic acid microspheres at room temperature using a membrane emulsification machine with a 5% polylactic acid dichloromethane solution as a dispersed phase and a 2% PVA aqueous phase solution as a continuous phase. The average particle size of the microspheres is 110 μm. The microspheres are then injected into the blood vessels of rat decellularized liver. The experimental results are shown in FIG. 5.

The elongated hydrogel microparticle embolic agent (length 620 μm, width 310 μm) prepared in Example 2 is injected into rabbit decellularized liver through a 200 μL pipette tip, and the embolization effect is observed, as shown in FIG. 4A to 4D. The scale bars in the figures are all 500 μm.

From the embolic effect comparison between the embolic agent prepared in Example 2 and that prepared in Comparative Example 1, it can be seen that the elongated hydrogel microparticle embolic agent in Example 2 is arranged in a straight line at blood vessel ends to achieve deeper embolization. Meanwhile, in large blood vessels, the elongated embolic agent in Example 2 is arranged traversely or by aggregating two elongated particles to achieve vascular embolization. In contrast, the spherical embolic agent in Comparative Example 1 is arranged loosely and irregularly in the blood vessels, and its contact area with the blood vessels is small. Accordingly, it may relatively easily detach from the embolization site.

It should be noted that the water-soluble polymer used in the above-mentioned embolic agent examples is polyvinyl alcohol. However, other water-soluble polymers, such as polyvinyl alcohol-based copolymers, polyethylene glycol, polyethylene glycol-based copolymers, etc., may also be used as water-soluble polymers for the preparation of embolic agents. In addition, the effect of these embolic agents may be equivalent to that of the embolic agent obtained by polyvinyl alcohol. This is not repeated herein.

The technical features of the above-mentioned exemplary embodiments and examples may be combined in any suitable ways. For the sake of brevity, other possible combinations of these technical features are not described herein. However, as long as there is no conflict in a combination of these technical features, it should be regarded as within the scope of the present disclosure.

It should be noted that the foregoing exemplary embodiments are merely intended for describing the technical solutions of the present disclosure, other than limiting the present disclosure. Although the present disclosure is described in detail with reference to the foregoing exemplary embodiments, a person of ordinary skill in the art should understand that changes and improvements may be made to the technical solutions described in the exemplary embodiments without departing from the scope of the present disclosure. Therefore, the scope of protection of the present disclosure is defined by the appended claims.

What is claimed is:

1. A method for forming an embolic agent, comprising:
obtaining an aqueous phase solution dissolved with a polymer to be cross-linked;
obtaining an oil phase solution containing a water-soluble organic cross-linking agent;
alternately injecting the oil phase solution and the aqueous phase solution into an elongated channel to form elongated droplets of the aqueous phase solution with uniform shape and size in the elongated channel, wherein the water-soluble organic cross-linking agent in the oil phase solution diffuses from the oil phase solution into the aqueous elongated droplets in the elongated channel, such that the water-soluble organic cross-linking agent and the polymer in the elongated droplets have a cross-linking reaction in the elongated channel to obtain solidified elongated and stable non-spherical hydrogel microparticles with uniform shape and size as the embolic agent; and
discharging the embolic agent from the elongated channel.

2. The method according to claim 1, wherein the alternately injecting of the oil phase solution and the aqueous phase solution into the elongated channel includes:
providing a microfluidic chip of a hydrophobic material and including the elongated channel; and
alternately injecting the oil phase solution and the aqueous phase solution into the elongated channel on the microfluidic chip.

3. The method according to claim 1, wherein
the elongated channel is arranged in a microfluidic chip; and
the cross-linking between the organic cross-linking agent dissolved in the oil phase solution and the polymer dissolved in the aqueous phase solution in the elongated channel is carried through thermal cross-linking.

4. The method according to claim 1, further comprising:
immersing the embolic agent discharged from the elongated channel into a collection solution; and
heating the collection solution under stirring, wherein the collection solution includes an oil-based solvent, and the elongated channel includes an inlet end and an outlet end.

5. The method according to claim 4, wherein a cross-linking agent is dissolved in the collection solution, such that the cross-linking agent and the embolic agent continue to react.

6. The method according to claim 4, wherein the heating of the collection solution under stirring is carried out at a temperature of 40° C. to 85° C.

7. The method according to claim 1, wherein
the elongated channel includes a first passage, a second passage, and a third passage;
the third passage is respectively in communication with the first passage and the second passage; and
the oil phase solution and the aqueous phase solution are respectively injected into the elongated channel through the first passage and the second passage and contact in the third passage to enable the cross-linking reaction in the aqueous phase solution.

8. The method according to claim 7, wherein the third passage includes an arched channel, and a straight channel in communication with the arched channel;

one end of the arched channel away from the straight channel respectively communicates with the first passage and the second passage; and the embolic agent is discharged from the straight channel.

9. The method according to claim 1, wherein a width and a height of the elongated channel are less than 1 mm.

10. The method according to claim 1, wherein a ratio of an injection rate of the oil phase solution to an injection rate of the aqueous phase solution is 20:1 to 2:1.

11. The method according to claim 1, wherein the aqueous phase solution further includes a catalyst; and in the aqueous phase solution, a mass fraction of the polymer is 2.5% to 7.5%, and a concentration of the catalyst is 0.25 mol/L to 0.75 mol/L.

12. The method according to claim 1, wherein the oil phase solution includes an oil-based solvent, a lipophilic emulsifier and the organic water-soluble cross-linking agent at a mass ratio of 1:(0.01-0.04): (0.075-0.3).

13. The method according to claim 1, wherein a volume of the polymer is reduced after solidification from the cross-linking reaction with the organic water-soluble cross-linking agent diffused from the oil phase solution into the elongated droplets.

14. The method according to claim 1, wherein the oil phase solution further contains an emulsifier to facilitate evenly dispersing the organic water-soluble cross-linking agent in the oil phase solution.

15. The method according to claim 1, wherein the organic water-soluble cross-linking agent comprises at least one of an aldehyde, an organic acid, or an organic acid anhydride.

* * * * *